(12) United States Patent
Soenksen et al.

(10) Patent No.: US 7,623,698 B2
(45) Date of Patent: Nov. 24, 2009

(54) METHOD OF LEARNING A KNOWLEDGE-BASED DATABASE USED IN AUTOMATIC DEFECT CLASSIFICATION

(75) Inventors: Dirk Soenksen, Schoeffengrund (DE); Ralf Friedrich, Giessen (DE); Andreas Draeger, Wetzlar (DE); Detlef Schupp, Herdorf/Dermbach (DE); Thin Van Luu, Wetzlar (DE); Wolfgang Langer, Wetzlar (DE)

(73) Assignee: KLA-Tencor MIE GmbH, Weilburg (DE)

( * ) Notice: Subject to any disclaimer, the term of this patent is extended or adjusted under 35 U.S.C. 154(b) by 499 days.

(21) Appl. No.: 10/564,454

(22) PCT Filed: Jun. 3, 2004

(86) PCT No.: PCT/EP2004/051008

§ 371 (c)(1),
(2), (4) Date: May 10, 2006

(87) PCT Pub. No.: WO2005/006002

PCT Pub. Date: Jan. 20, 2005

(65) Prior Publication Data

US 2006/0245634 A1      Nov. 2, 2006

(30) Foreign Application Priority Data

Jul. 12, 2003   (DE)   ................. 103 31 646
May 7, 2004     (DE)   ............. 10 2004 022 717

(51) Int. Cl.
    *G06K 9/00* (2006.01)
(52) U.S. Cl. .................. 382/145; 382/149; 715/835; 715/837; 356/237.1
(58) Field of Classification Search ............. 382/149, 382/145, 224, 159, 144; 719/310, 315; 715/744, 715/835, 837, 764, 841, 210, 839, 762, 809, 715/804, 973, 708, 250, 866; 714/E11.21; 700/110, 121, 103; 702/82, 83, 35, 81; 438/14, 438/16, 17, 18; 364/552, 468.7; 148/33; 365/552; 710/110, 121, 103; 348/125, 86, 348/87; 356/237.1, 237.2, 237.3, 237.4, 356/237.5; 250/559.01; 717/109, 113, 108
See application file for complete search history.

(56) References Cited

U.S. PATENT DOCUMENTS

| | | | | |
|---|---|---|---|---|
| 6,104,835 A | * | 8/2000 | Han | 382/225 |
| 6,292,582 B1 | * | 9/2001 | Lin et al. | 382/149 |
| 6,408,219 B2 | * | 6/2002 | Lamey et al. | 700/110 |
| 6,456,899 B1 | * | 9/2002 | Gleason et al. | 700/212 |
| 6,483,938 B1 | * | 11/2002 | Hennessey et al. | 382/149 |
| 6,792,367 B2 | * | 9/2004 | Hosoya et al. | 702/83 |
| 6,973,209 B2 | * | 12/2005 | Tanaka | 382/149 |

* cited by examiner

*Primary Examiner*—Sheela C Chawan
(74) *Attorney, Agent, or Firm*—Simpson & Simpson, PLLC

(57) ABSTRACT

The invention relates to a method of learning a knowledge-based database used in automatic defect classification. According to this method, the user is spared a series of entries as the system carries out an automatic learn mode, which requires a reduced number of user entries.

14 Claims, 15 Drawing Sheets

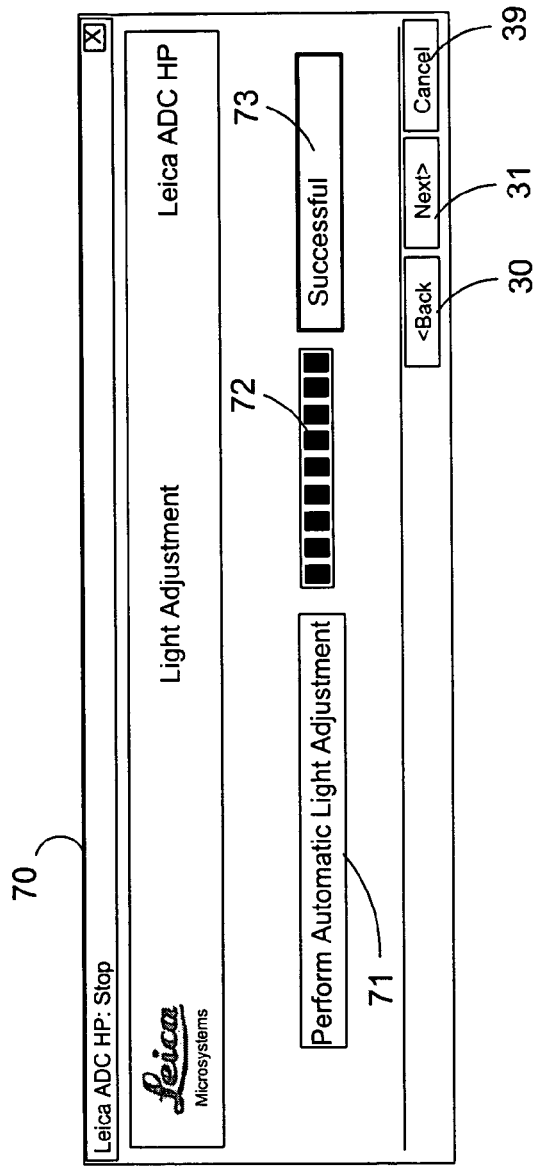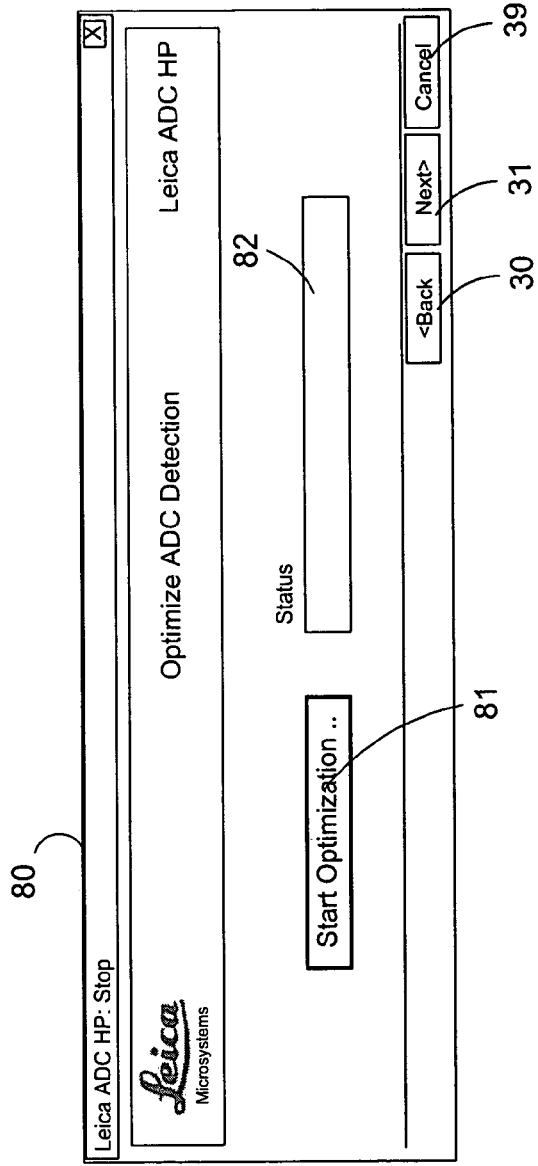
Fig. 9
Fig. 10

Fig. 22

Table Print Preview

Easy ADC Report (Advanced)

| Argument: | Value |
|---|---|
| File Information: | |
| Output File: | W:\Program Files\LEICA-MEL\VisconNT\Data\Review\Kla\Analog-Devices\KlaFile |
| Recipe Information: | |
| EasyADC Recipe: | W:\Program Files\LEICA-MEL\VisconNT\Data\Review\LDTB39401X1-POLY1-YD |
| KB File Name: | W:\Program Files\LEICA-MEL\VisconNT\Data\Review\Kla\Analog-Devices\KlaFile |
| Autoalignment: | W:\Program Files\LEICA-MEL\VisconNT\Data\Review\Kla\Analog-Devices\KlaFile |
| Focus: | W:\Program Files\LEICA-MEL\VisconNT\Data\Review\LDTB39401X1-POLY1-YD |
| Knowledge-Base Information: | |
| Objective: | 100x-PLAPO 100x0.90 BD |
| Contrast: | BF |
| Focus: | VIDEO |
| Aperture: | 3 |
| Intensity [%] | 85 |
| Statistic Information: | |
| Wafers: | 1 |
| Total Defects: | 128 |
| Classified Defects: | N/A |
| ADC Classes: | N/A |
| Defects/Class: | N/A |
| Defects Detached: | N/A |
| Redetection [%] | N/A |

Easy ADC Report (Advanced)   Page 1

180

METHOD OF LEARNING A KNOWLEDGE-BASED DATABASE USED IN AUTOMATIC DEFECT CLASSIFICATION

CROSS REFERENCE TO RELATED APPLICATION

This application claims the benefit of International Application PCT/EP2004/051008, filed Jun. 3, 2004, which claims priority from German Application 103 31 646.9, filed Jul. 12, 2003.

BACKGROUND OF THE INVENTION

The invention relates to a method for teaching a knowledge-based database for automatic defect classification.

In semiconductor manufacturing, wafers or masks are processed sequentially in a number of process steps during the manufacturing process. With increasing integration density, the demands of the quality of the structures formed on the wafers increase. In order to check the quality of the structures formed and to be able to find possible defects, the demand for quality, precision, and reproducibility of the components and process steps used with the wafer is critical. This means that during production of a wafer with a number of process steps, a reliable and early recognition of defects is especially important. In this process, it is necessary to classify the defects that occur in order to thus achieve a fast processing and testing of the wafers.

In earlier versions of "Automatic Defect Classification" (ADC), it was necessary to proceed with a manual classification of the defects on a wafer or on a mask. The teaching of a knowledge base was thus extremely time consuming.

SUMMARY OF THE INVENTION

The object of this invention is to provide a method with which a simple and fast possibility is offered for creating all the data and files (knowledge base, auto alignment, focus setup) necessary for an "ADC run."

This object is achieved by a method of learning a knowledge-based database for automatic defect classification wherein a review data file is selected, and parameters and data are input by a user on one page of a learning mode, where the parameters and the data are known to the user. Additionally, an alignment procedure and a procedure for adjusting light intensity are used. Optimal light intensity is automatically adjusted by approaching a few defects and if necessary regulating the optimal illumination. Detection is checked using a few examples wherein the optimization of the detection parameters is carried out using pictures. Respective defects are detected and a descriptor is assigned to the respective defect by automatically approaching all defects of a wafer or wafers. Descriptors of the defect are then analyzed and automatically grouped.

It is especially advantageous that Leica ADC HP offers a simple and fast option for creating data and files (knowledge base, auto alignment, focus setup) for an ADC run. To do this, in part specified data and files are used. Since a manual classification of the defects on a wafer is no longer necessary, as in earlier ADC versions, the time needed to create a new ADC protocol for teaching a knowledge base can be reduced by up to 50%. Additionally, in many cases the quality of the knowledge base improves because of the "pregrouping function" that is included, which in turn has a direct influence on the precision of the ADC run. ADC HP is described as an independent "learn mode". In individual steps, the user must specify, confirm and if necessary change the required data. The individual steps are shown as separate pages in the Leica ADC HP dialog. The user prompts for the individual pages are in the so-called wizard style, i.e., using <Back> and <Next> buttons. In contrast to the previous learning mode, the new learning mode has the advantage that it is uncomplicated and requires a reduced number of steps that have to be carried out by the user in the proper sequence. In the previous learning mode, preclassified defects were required. All the new learning mode needs is one or more wafers with as many unclassified defects as possible.

Since during a few of the steps an interaction with the Viscon interface is necessary, the Leica ADC HP dialog is not displayed modally, but top-most. The dialog can automatically be hidden or the user can make it hidden or visible again.

The input of parameters and data includes the selection of the elements present on the semiconductor substrate, whereby it is possible for memory circuits, logic circuits, and a blank wafer without resist or with resist to exist as elements. The parameters or data of the layers on the wafer include the data of a polymer layer, of an oxide layer, of a contact or of a metal layer.

The user selects the illumination type, at least one lens and a focus type. For the illumination type, bright field, UV or DUV can be selected. The default setting is bright field, and the default for the lens is 100× magnification.

A manual two-point alignment is carried out, whereby a first point is aligned manually by approaching a table. During the learning of the first point, data is automatically stored for the auto alignment file. Each alignment point is learned with three different magnifications of the lens. The adjustment of the optimal intensity of illumination is carried out by random selection of a specific number of defects. Then the selected defects are approached and a picture is taken of each defect. A starting value for the brightness of illumination and the adjustment of the illumination is achieved using a histogram evaluation of the pictures. Defects that are no larger than 25% of the video image width and height are used to adjust the optimal intensity of the illumination.

Twenty defects will be used to adjust the intensity of illumination. Of the defects on the wafer that are approached, pictures are taken and stored temporarily until pictures are taken of all defects. After all the pictures have been taken, they are shown on the display as thumbnails. A few thumbnails are rejected if the thumbnails exceed a threshold value for the focus. The analysis and automatic grouping of the descriptors of the defects divides the thumbnails of the defects that have been produced into groups. On the display, the first nine examples of a selected group of defects in a thumbnail representation are shown.

BRIEF DESCRIPTION OF THE DRAWINGS

In the following, the invention will be explained in more detail using embodiment examples that are shown schematically in the figures. The same reference numbers in the individual figures refer to the same elements. The following are shown in detail:

FIG. 9 shows a page of the learning mode by which the user carries out an automatic light adjustment;

FIG. 10 shows a page of the learning mode by which the user achieves an optimization of the adjustment of the detection parameters;

FIG. 22 shows a representation of the printed Easy ADC Report.

DESCRIPTION OF THE PREFERRED EMBODIMENTS

Figure 1:
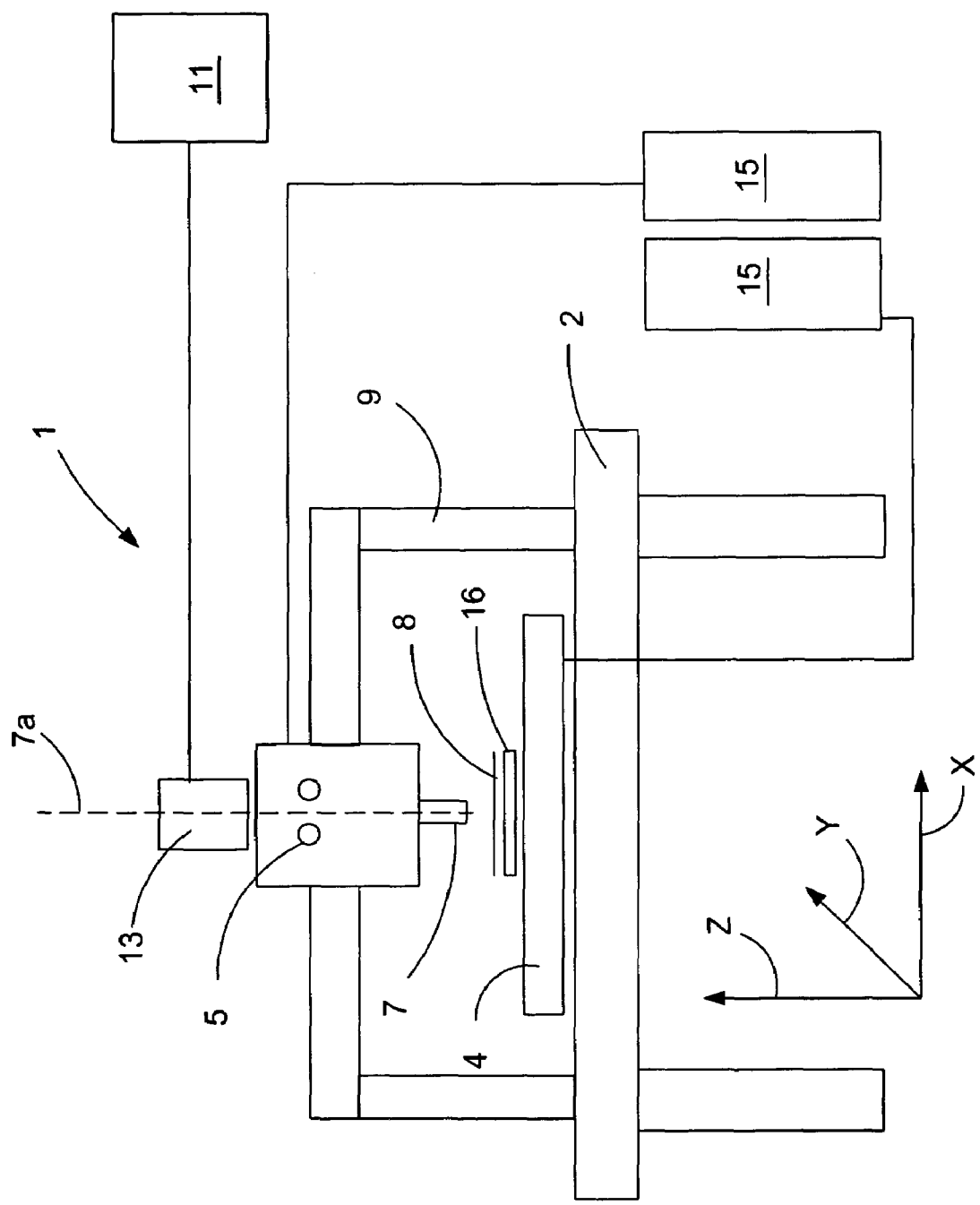
FIG. 1 shows a schematic structure of a wafer inspection device as an overview in which the method according to the invention is implemented.

FIG. 1 shows a schematic structure of a wafer inspection device 1 as an overview, in which the method according to the invention is implemented. On a base frame 2, scanning table 4 is integrated as a placement table for wafer 8. Scanning table 4 can be driven in an X-coordinate direction and a Y-coordinate direction. Wafer 8 to be tested is placed or hooked on scanning table 4. An observation device that is preferably equipped with a microscope lens 7 is connected to base frame 2 by way of a carrier unit 9. Microscope lens 7 makes possible the enlarged observation of wafer 8. Several microscope lenses 7 can be provided on a revolving unit (not shown) so that observation with different enlargements is possible. The structures of wafer 8 that are observed when they are enlarged can be observed directly using eyepiece 5 or by way of a display 11 that is connected to a CCD camera 13. Additionally, electronic unit 15 is provided with which a system automation can be achieved. In particular, electronic unit 15 is used to control scanning table 14, for reading out camera 13 and for controlling display 11. Wafer holder 16 is usually designed in such a way that it can hold wafer 8 to be tested so that it is fixed during the testing period. Scanning table 14 is designed so that it can be driven in each perpendicular X-coordinate direction and one Y-coordinate direction. In this way, each point to be observed on wafer 8 can be brought under optical axis 7a of microscope lens 7 (FIG. 1).

Figures 2, 3:
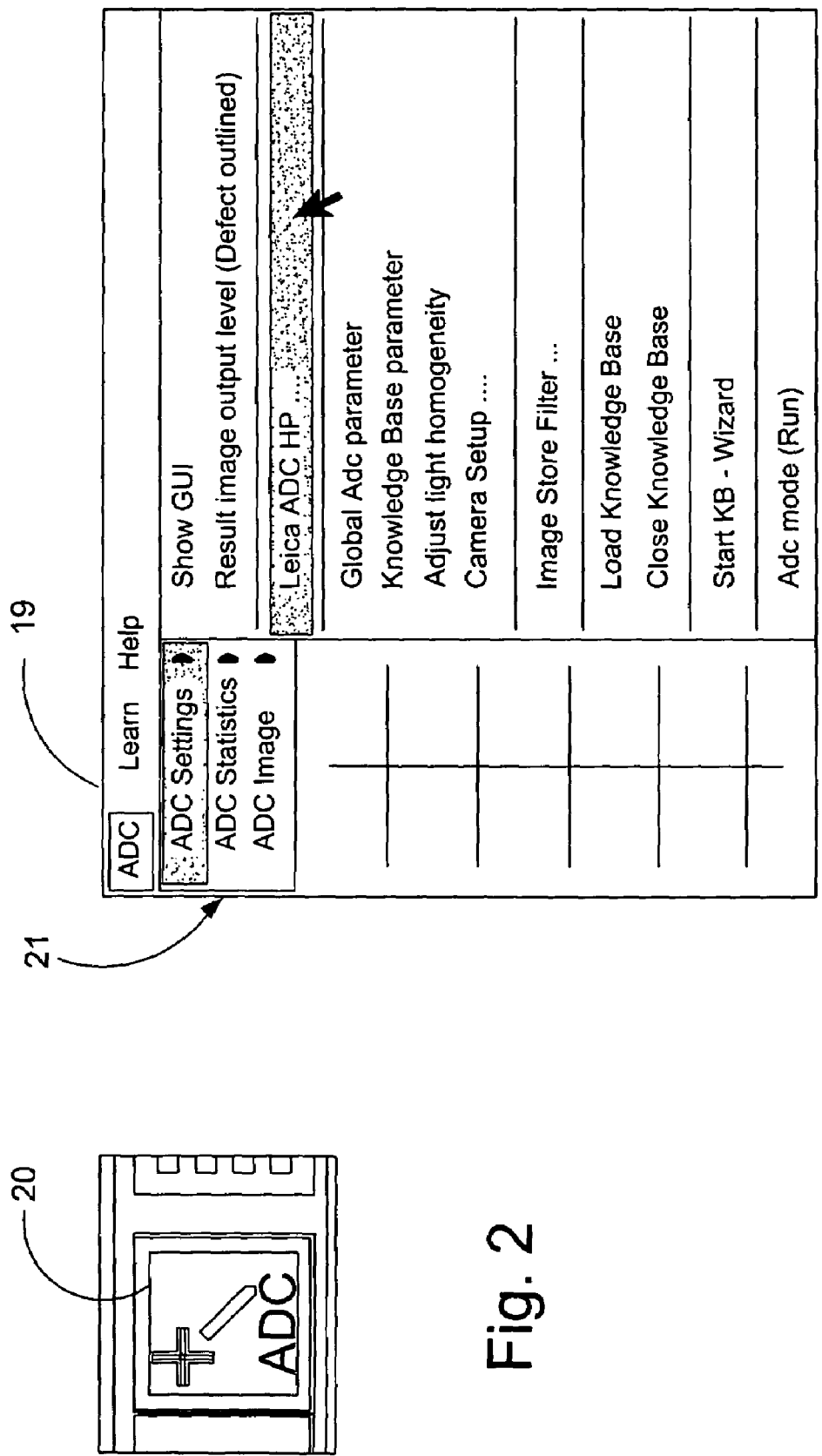
FIG. 2 shows the ADC HP toolbar button with which the user calls the function for automatic defect recognition.
FIG. 3 shows the ADC HP call of the "ADC" menu.

FIG. 2 shows ADC HP toolbar button 20, with which the user calls the function for automatic defect recognition. The ADC HP dialog is called using "ADC" HP toolbar button 20 or using main toolbar 19 of Viscon application 21 in "ADC" menu or in the context menu of the "ADC" dialog (see FIG. 3). Every user (starting from the "operator" user level) has access to this menu entry. Since ADC HP is a separate option, the menu entry is only visible if ADC HP is also installed. This option is protected, as before, using a registry entry that is generated by the installation program when this option is selected. If a program is already loaded in Viscon, the menu entry will be shown deactivated.

Figure 4:
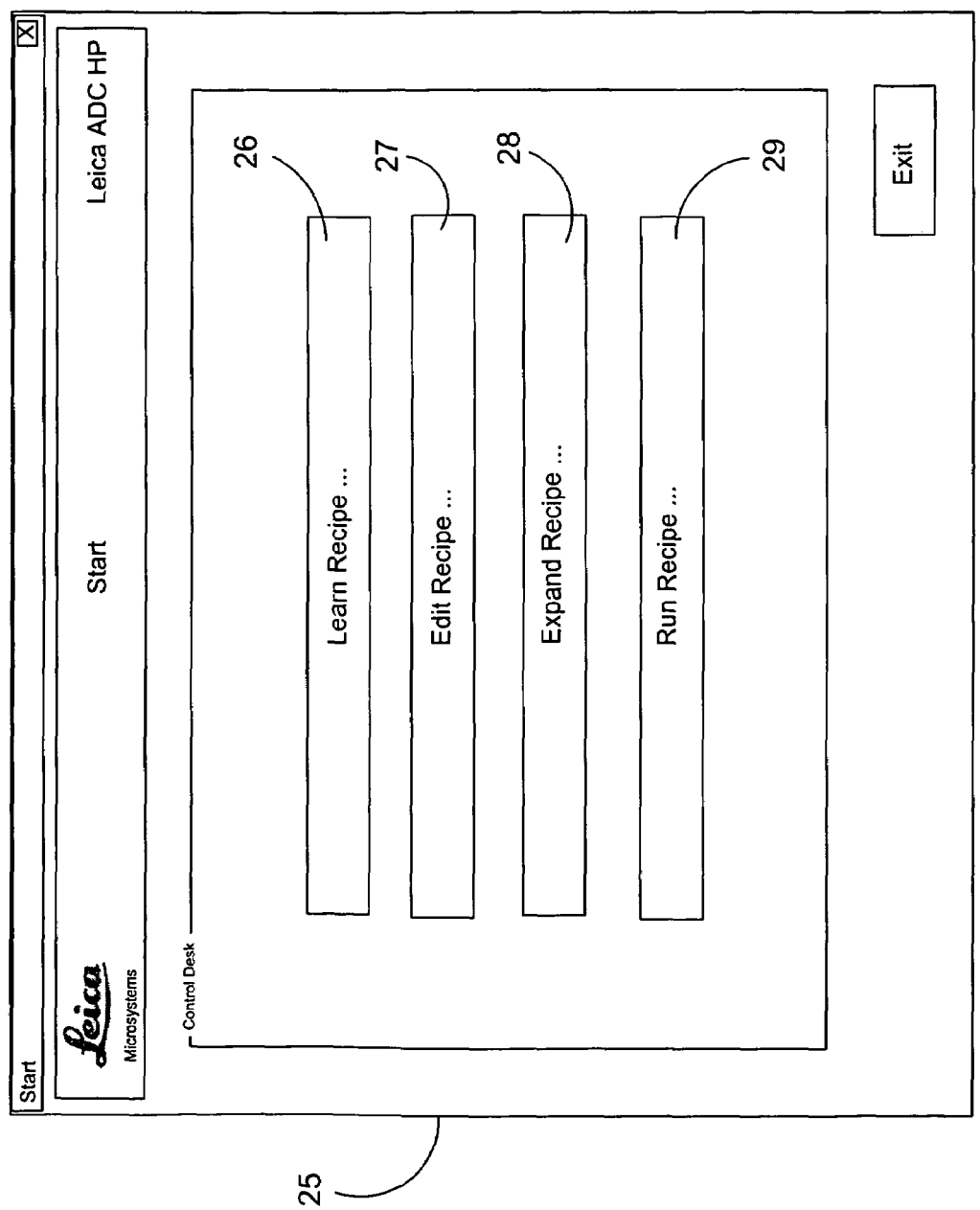
FIG. 4 shows a "Leica ADC HP Control Desk" window that clearly summarizes, in one window, the ADC tasks that are already partially available in earlier ADC versions.

FIG. 4 shows "Leica ADC HP Control Desk" window 25. It combines the ADC tasks, some of which were already available in earlier ADC versions, clearly in a window and is used as the starting basis to start individual modules 26, 27, 28, and 29. In detail, this includes:

"Learn recipe": learning and creation of a new ADC recipe and a knowledge base with subsequent ADC run (run recipe), "Edit recipe": for processing an available knowledge base, "Expand recipe": for expanding an available knowledge base and "Run recipe": to start an ADC run.

One button is provided for each of the individual modules. In the current embodiment, this includes "learn recipe"—button 26, "edit recipe"—button 27, "expand recipe"—button 28 and "run recipe"—button 29. When individual buttons 26, 27, 28, 29 are actuated, the individual tasks are executed. Those tasks that were already present in the earlier ADC version will only be discussed briefly here.

"Edit recipe": After pressing is button 27, the user has to select an available knowledge base file. This is started by the external application "KB Wizard" and the contents of the file are displayed. The data can be processed there and the knowledge base as a whole can be tested.

"Expand recipe": With button 28, the user selects an available knowledge base file and a review data file. During the subsequent ADC run, new data are collected and temporarily stored in the background. Once the run is completed, the temporary data and the knowledge base (KB) file used will be loaded by the "KB Wizard" application and displayed. The user can now take the new data selectively over into the knowledge base.

"Run recipe": By selection of button 29, a review data file and an ADC recipe will be selected and an ADC run will be started. All defects selected by the user will be detected automatically and classified using the knowledge base file noted in the ADC recipe. The results will be written again at the end as a review data file.

The task connected with the actuation of "learn recipe"—button 26 will be described in detail in the following.

The ADC HP learning mode is displayed as a non-modal dialog. The user must input the necessary data and/or select files in eight successive steps, i.e. on eight pages. The last page only represents the result of the ADC HP learning process.

Figure 5:
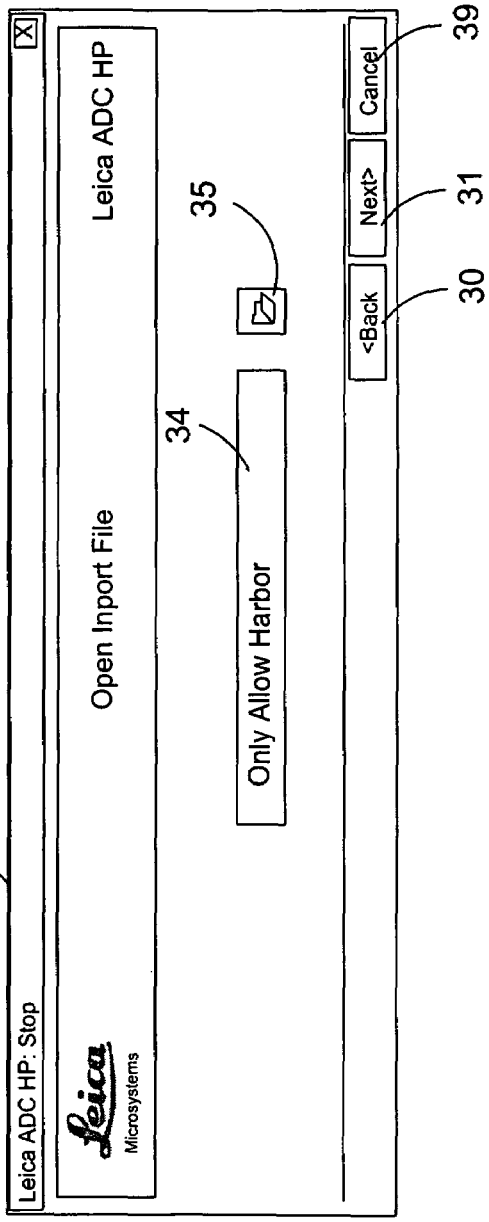
FIG. 5 shows a page of a learning mode that the user calls up and in this process an input file opens, i.e., specifies a review data file.

To do this, the user can use <Back> and <Next> buttons 30, 31 (wizard style), as long as the current status allows it, to go to the previous or to the next step (see FIG. 5).

In general, it is true that the display of the individual pages is not user-level-dependent. The exceptions are additional user interface elements that are only visible to the development user level. These are now visible during the development phase and will be removed in the release version and be generally invisible for all user levels.

FIG. 5 shows page 33 of the learning mode that the user calls up and thereby opens an input file 34, i.e., specifies a review data file. Page 33 is designated with "open input file." On page 33, the data file is displayed (without path). Using file open button 35, the directories are displayed for the user for data input. If an input file has been determined, it is temporarily opened, but the Viscon sequencer is not started.

The file "EasyADCLearn.vsl" is used as the script file, hard coded. The necessary data for LotId (lot identification), WaferId (wafer identification), StepId (step identification) and SetupId (setup identification) of the first wafer are read out from the open file. Then the file is closed again. Any standard settings (e.g. Auto Start) are not affected by the process and/or will be put back to the original status. The user can cancel the procedure with a cancel button 39.

Figure 6:
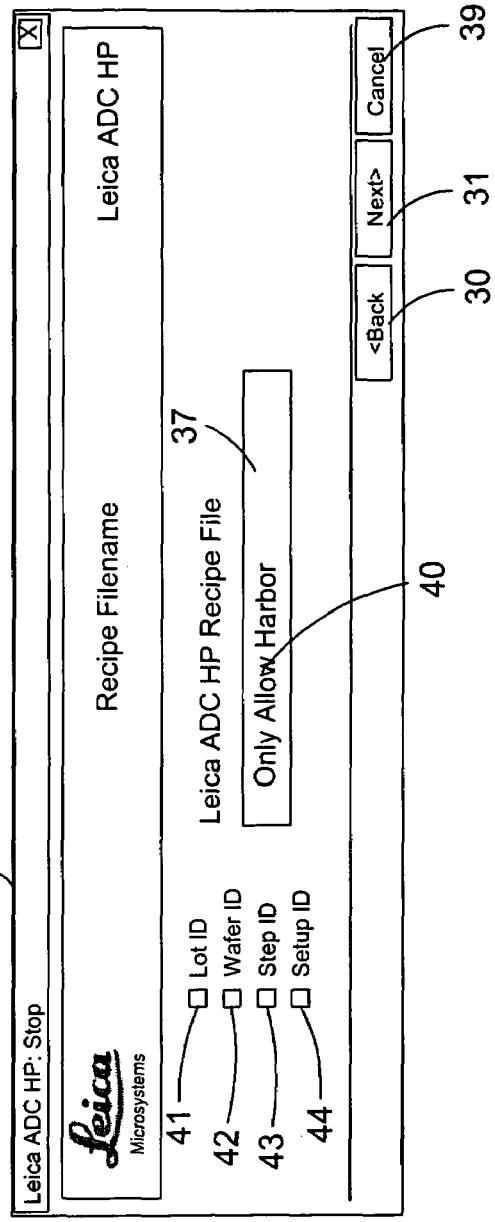
FIG. 6 shows a page of the learning mode that the user calls and thus assigns a name for a "recipe file"

FIG. 6 shows page 38 of the learning mode that the user calls up and thereby assigns a name for a recipe file. Page 33 is designated with "recipe file." Actuating back button 30 is not allowed in page 38. Actuation of next button 31 is allowed if a valid input file 37 has been selected. The user can cancel the ADC HP learn mode with cancel button 39. The Leica ADC HP recipe file is displayed in edit box 40. The previously read name components are summarized according to specification, and the resulting file name (with the extension ."vsl") is displayed. The name components are separated by a "_" symbol (underscore).

Invalid letters in the resulting file name will be removed and hyphens will be replaced with underscores. The user also has the option of changing the specified name (completely or partially) as desired. The file "EasyADCRun.vsl" is used as a template for the resulting recipe file (sequence control file during an ADC run) (hard coded). Page 38 contains several checkboxes 41, 42, 43 and 44. Checkboxes 41, 42, 43 and 44 are used to determine the name components. In this case, LotID, StepID and SetupId are used as defaults. The resulting file name (without the extension ."vsl") is also used as a default for other files (auto alignment, focus setup file, etc.). The data file of the results "result data file" is always written with the same name as the input file and the same format type and in the standard result directory. Back button 30 is permitted and next button 31 is permitted if at least one name component has been selected. Cancel button 39 is permitted.

Figure 7:
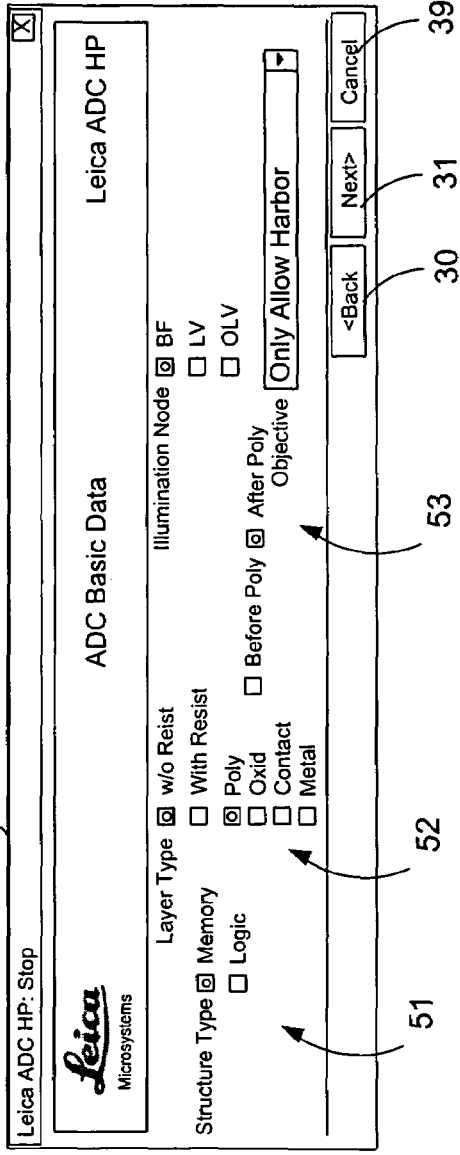
FIG. 7 shows a page of the learning mode by which the user specifies the ADC knowledge base data.

FIG. 7 is shows page 50 of the learning mode by which the user specifies data for the ADC knowledge base. Page 50 is designated as "ADC basic data." In selection column 51 with the designation "structure type," the user can choose between "memory" and "logic." An additional selection or a blank, unstructured wafer "bare wafer" is also possible. To determine the ADC run mode (repetitive or random mode) and/or auto alignment modes (normal auto alignment or bare wafer alignment), the procedure is according to the selection. The default setting is set to "logic."

In selection column 52, which has designation layer type, the user can select whether one or more layers will be applied to the wafer. Also of interest is which layers will be applied to the wafer. Without resist is "w/o resist," with resist is "with resist" (see FIG. 7). The resists, or also other layers, are applied on wafer 8 or the semiconductor substrate. The default setting is "w/o resist."

In other setting options, the user can select the layer type. A polymer layer is designated with "poly," an oxide layer with "oxide," a contact with "contact" or a metal layer with "metal." The sequence of application of the different layers can also be selected. For example, an oxide layer (oxide) is applied before the polymer layer, this is designated with "before poly." The selection of the layer type metal allows the user the choice between a single metal layer (metal 1), a double metal layer (metal 2) and an n-fold metal layer (n-metal). The determination of whether a main layer or a subordinate layer is involved, is used to determine the random mode and the focus type. The default settings for the layers are "poly," for "oxide": before poly and for "metal": metal 1. Oxide and metal sub-layer radio boxes are only activated if "oxide" or "metal" has previously been selected. Otherwise they are shown deactivated. In selection column 53, the user can select the "illumination mode." The radio boxes with the designation BF for bright field, UV for ultraviolet and DUV for deep UV are available to the user. In a list box 54, the lenses that are available are displayed to the user, whereby only the lenses that fit the selected ADC type are displayed. The default setting is bright field "BF," and a lens with 100× or lower magnification is suggested.

The following table (Table 1) shows the resulting focus setting using the selected data:

| Layer/ADC type | Focus type | Offset value for TV focus |
| --- | --- | --- |
| Poly | TV focus | 400 |
| Poly resist | TV focus | 0 |
| Oxide before poly | Laser | — |
| Oxide before poly resist | TV focus | 0 |
| Oxide after poly | TV focus | 2000 |
| Oxide after poly resist | TV focus | 2000 |
| Contact | Laser | — |
| Contact resist | Laser | — |
| Metal 1 | TV focus | 1500 |
| Metal 1 resist | TV focus | 0 |
| Metal 2 | TV focus | 1800 |
| Metal 2 resist | TV focus | 0 |
| n-Metal | TV focus | 2500 |
| n-Metal resist | TV focus | 0 |

For TV focus, the default values of the "TV Focus Flexible 2" mode are used. Back button 30, next button 31 and cancel button 39 are permitted in this window. If next button 31 is pressed, the ADC HP dialog becomes invisible.

A copy of the "EasyADCLearn" files is created and specific actions are adapted (auto alignment) and data (grab setup).

The same changes are made for the named copy of the "EasyADCRun" file (the later ADC run recipe). The input file is loaded with the adapted script file, and the Viscon NT sequencer is started. The file is automatically processed up to wafer selection. The standard wafer selection dialog is used and displayed.

As a default, all available wafers are selected (default setting in easy ADC script file).

Figure 8:
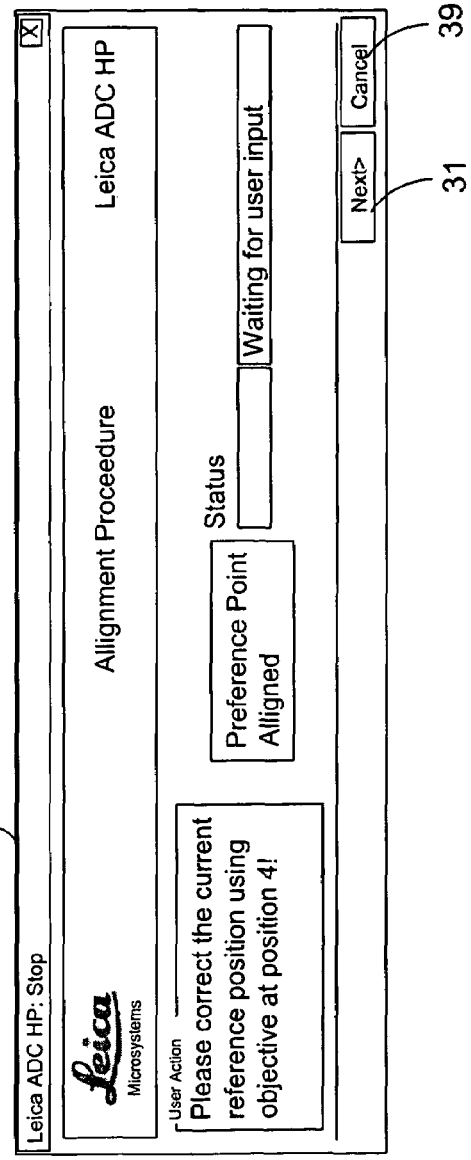
FIG. 8 shows a page of the learning mode by which the user carries out the teaching and an automatic alignment.

FIG. 8 is a page 60 of the learning mode, by which the user carriers out the teaching and an automatic, or at least semi-automatic, alignment, page 60 is designated as "alignment procedure." After actuation of the wafer selection by the user, the first wafer is loaded and the file is processed up to auto alignment. Depending on the setting of the layers present on the wafer, the learning mode of the corresponding auto alignment will be started (semi-auto or later bare wafer alignment). The user can carry out a manual two-point alignment whereby only the very first point is aligned manually (driving of the table using joystick or by mouse double click in the live video image) and confirmed. During the teaching of the first point, data is automatically stored for the auto alignment file. Each alignment point is taught with three different lens magnifications, whereby the highest magnification lens is specified by the selection on page 50 (ADC basic data).

The second point is already taught and aligned automatically using the stored data of the first point. The selected ADC lens is always specified by the software. This lens must be used since it will be needed for the later light adjustment (method used: alignment point).

If the learned structure of the first input point is not found on the second alignment point, the second point will be "offset" toward the center point of the wafer and the structure will be searched again. The second point is "offset" by a maximum of six dies before the alignment aborts with a defect. In this case, an information window will be displayed to the user that says that the alignment has been aborted and the wafer is discharged.

After the end of the alignment, the Viscon sequencer is paused (incorporated pause action (without message box display) in the easy ADC script file), the ADC HP dialog becomes visible again and displays the next page. Next button 31 is not permitted if alignment is carried out and/or has been aborted due to a defect. Next button 31 is permitted if the alignment was successful. Cancel button 39 is permitted and cancels the entire ADC HP learning mode.

FIG. 9 is page 70 of the learning mode by which the user carries out an automatic light adjustment. This page is designated as "light adjustment." After pressing a "perform automatic light adjustment" button 71, a specific number of points (defects from the data file) will be selected randomly. If size information is available, only defects will be selected that are greater than 25% of the video image width and height. These defects are approached and pictures are taken. A "lamp brightness" start value is determined using histogram evaluation and adjusted at the microscope. This means that the brightness will be regulated down so that no defect image is "overwritten." To do this, all available color channels will be tested and adjusted in an appropriate way.

Then an automatic light adjustment is carried out. If it is successful, the data obtained will be stored in the knowledge base file. As a default, 20 points (defects) are used for the "starting value" determination and the "alignment" method of the light adjustment is used.

Page 70 contains Statusbox 72 ("progress control box") and Infobox 73 "read only edit box." During the automatic light adjustment, the progress is displayed in Statusbox 72. A status text is displayed in Infobox 73 whether this is successful or unsuccessful. Back button 30 is not permitted when the light adjustment is being carried out. Back button 30 is permitted if the light adjustment is rejected. The wafer is discharged, and page 50 "ADC basic data" is displayed. Next button 31 is permitted if the light adjustment was successful. The cancel button is permitted if light adjustment has been carried out and in this process all open files were closed and deleted.

FIG. 10 is a page 80 of the learning mode, by which the user achieves an optimization of the setting of the detection parameters. Page 80 is designated as "optimize ADC detection." The process is started using a button 81, which is designated as "start optimization." The optimization function will ensure that the standard values for focus adjustment and detection parameters function on the selected wafer. If this is not the case, the user has the option here again of changing the specified standard values. After button 81 is pressed, the Viscon sequencer is started, defects are selected, approached and pictures are taken. The text on button 81 then changes into "stop optimization." The progress of the picture taking is displayed in a status box 82. The user can then cancel the procedure by pressing it again. If all the necessary pictures have been taken, they will be displayed in another dialog in an additional representation on the screen as thumbnails. Ten defects (hard coded) are used for optimization. The number can be changed using a registry entry and/or development user level. Back button 30 is not permitted if the detection optimization is being carried out. Next button 31 is not permitted if the detection optimization is carried out. Cancel button 39 is not permitted if the detection optimization is carried out.

By pressing <Start Optimization> button 81, the Viscon sequencer is started again, the button text changes to "stop optimization" and a specified number of defects of the current wafer is selected.

The defects are approached and in this process a special ADC action is initiated. This action takes the pictures, detects the defects using an ADC routine that is already developed and stores the pictures temporarily until pictures of all the defects have been taken. The progress of this procedure is displayed by means of the status box. During picture taking, the user can cancel the procedure by repeatedly pressing the button.

Figure 11:
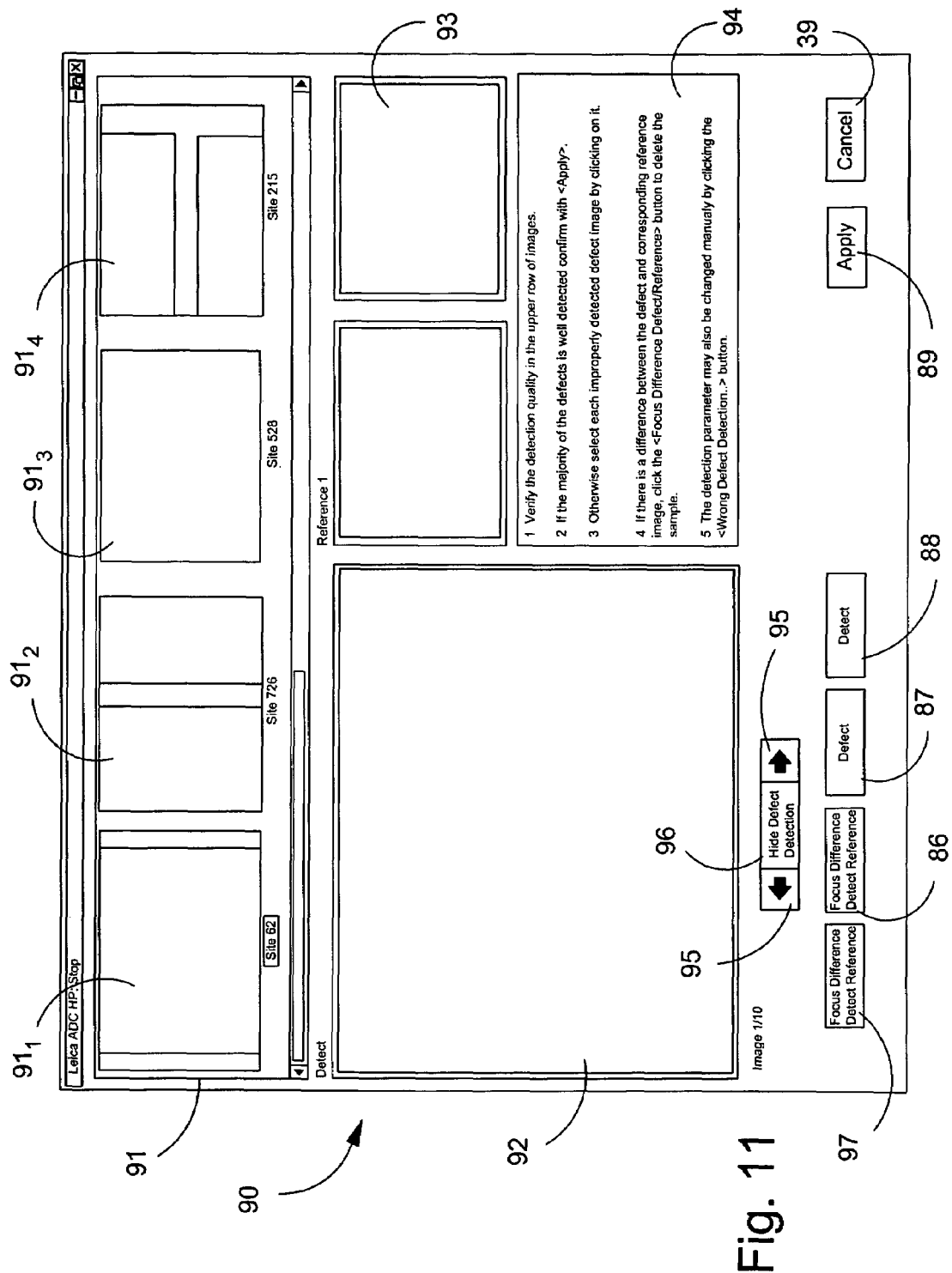
FIG. 11 shows a representation of the thumbnails on the screen.

FIG. 11 shows a representation of several thumbnails $91_1$, $91_2$, $91_3$, ..., $91_n$ on display 11. If all pictures have been taken, the ADC HP dialog is switched to invisible and the pictures are displayed in a thumbnail dialog 90 (complete picture display on the screen). The Viscon sequencer pauses at this time.

Thumbnail dialog 90 is basically divided into first area 91, second area 92, third area 93 and a fourth area 94. First area 91 comprises a horizontal list in which thumbnails $91_1$, $91_2$, $91_3$, ..., $91_n$ are represented with detection marking and defect ID (defect identification). The currently selected picture is shown in second area 92 with a maximum resolution of 640×480 pixels. If available, the reference pictures are also shown, reduced, in third area 93. The current picture selection can be changed using a mouse click, cursor keys and/or browse buttons 95 under the defect picture.

The defect marking can be switched off and back on again using <Hide Defect Detection> button 96. Browse buttons 95 are used for selection and display of the next or the previous defect picture. <Hide Defect Detection> button 96 is designed as a toggle button, and in this way the detection marking can be made visible or invisible.

Figure 12:
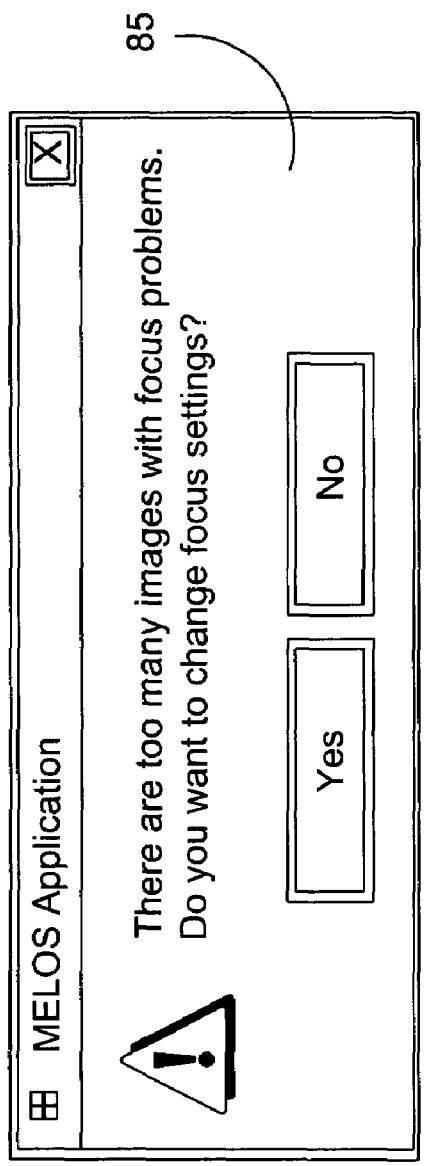
FIG. 12 shows a representation of a message box.

Focus difference—defect/reference button 97 makes it possible to display a message box 86 (see FIG. 12). During operation, the selected defect picture (and available reference pictures) will be thrown away, i.e., deleted from the display. If an internal threshold value (default: 30%) of the unsatisfactory pictures thrown away (bad focus pictures) is exceeded, the focus values are changed (i.e., change from laser to TV focus or change of the TV focus offset in 500 nm steps). The defects are then approached again and data recorded. To do this, thumbnail dialog 90 is closed and the ADC HP dialog will be displayed again during the scan procedure.

Wrong defect detection button 86 makes it possible for the detection threshold for the selected picture to be determined again. To do this, a new dialog 80 is displayed (see FIG. 10).

Refresh button 87 makes it possible for the average value of the threshold of all pictures in the list to be determined, and all detections will be recalculated with this new average value. The list will then be set up again. Pictures with "autothreshold" (−1) are not used to determine the average value.

Default button 88 makes it possible for all the changes in the detection parameters of all pictures to be reversed. The list is set up again with the original values.

The dialog is closed with an apply button 89, the average value of the threshold is calculated and taken over as a global detection parameter. Pictures with "autothreshold" (−1) are not included for determining the average value. The optimized dialog is closed, the ADC HP dialog is switched so that it is visible again and the new overall detection threshold is entered in the knowledge base.

Cancel button 39 closes the optimize dialog, and the ADC HP dialog becomes visible again. All changes are rejected.

Figure 13:
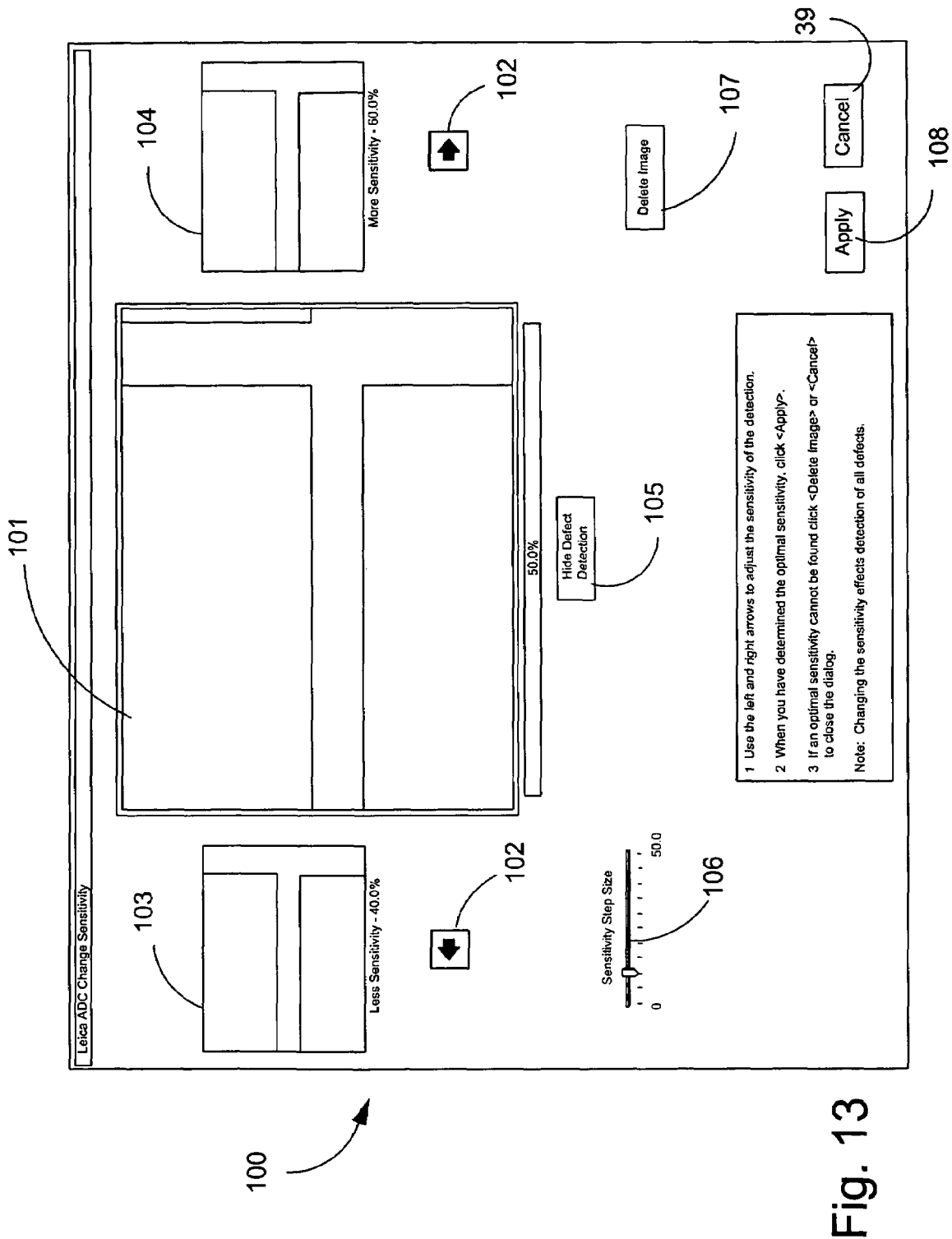
FIG. 13 shows a representation of a change sensitivity dialog.

FIG. 13 is an illustration of a dialog 100 for "change sensitivity." Dialog 100 is used to determine the optimum setting for the detection threshold of the selected defect picture. Defect picture 101 is displayed centrally with the associated detection threshold in dialog 100. If indirect automatic detection threshold has been used due to prior adjustments (on page 50 "ADC Basic Data"), a value of 50% is assumed.

The sensitivity of the detection can be reduced or increased using two buttons 102. Defect picture 101 shown in the center shows the defect recognition with the currently selected sensitivity. The value is shown under defect picture 101. Reduced picture 103 is shown on the left next to defect picture 101 and shows the change in detection with reduced sensitivity. Also, reduced picture 103 is shown at the right next to defect picture 101 and shows the change of the detection with increased sensitivity. By clicking with the mouse on one of the reduced pictures and/or by pressing on the buttons 102 lying under them, the current sensitivity is changed to this value and the picture is now shown in the center. The changes on the left and right will then be recalculated.

Hide defect detection button 105 is designed as a toggle button. In this way, the detection marking is switched to visible or invisible.

Slider 106 with the designation "sensitivity step size" is used to change the magnitude of changes of sensitivity during actuation of button 102. Delete image button 107 is used to reject a defect for further evaluation. The defect is removed from the list of the optimization dialog. This dialog is closed, and the user goes to the previous dialog.

Figure 14:
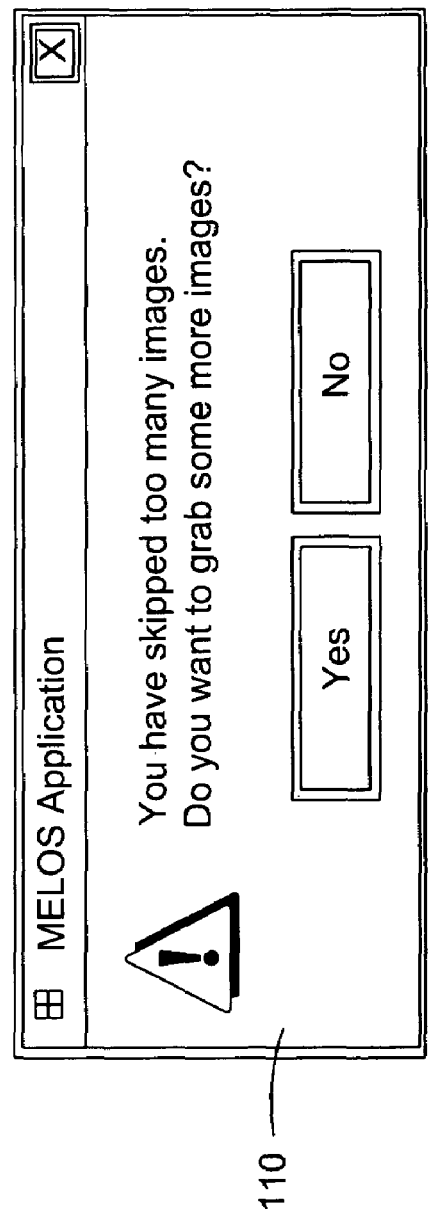
FIG. 14 shows a representation of a window that gives the user a warning message.
Figure 15:
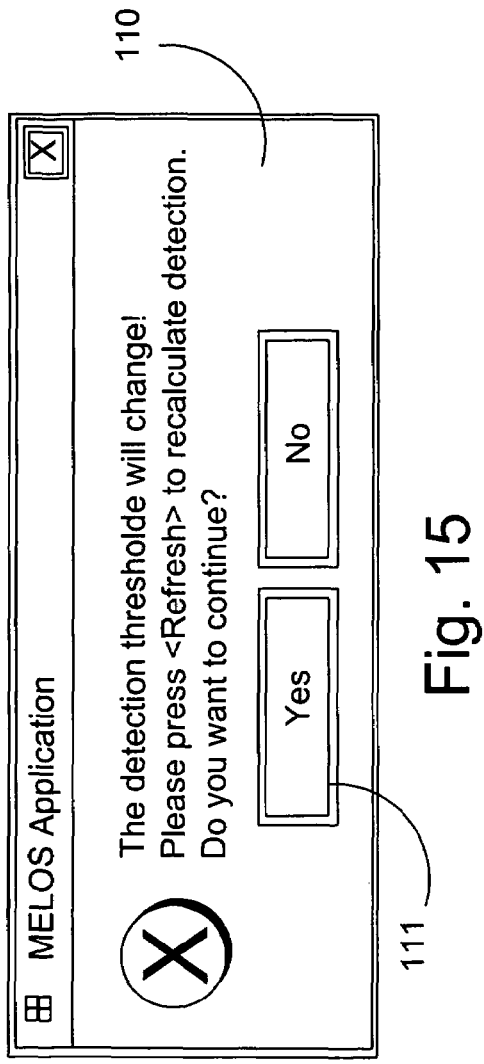
FIG. 15 shows a representation of an information window for acceptance of the new detection threshold.

FIG. 14 is a representation of a window 110 that gives the user a warning message. If an internal threshold (default: 30%) of the "wrong detection" pictures rejected is exceeded, new defects can be selected (automatically), approached and data recorded. Apply button 107 starts the application. FIG. 15 is a representation of information window 110 for acceptance of the new detection threshold. The information window informs the user that by acceptance of the new detection threshold the detection of all the other pictures will also change. The new value will be applied to all other pictures by pressing on <Refresh> button 87 in optimize dialog 90.

By operating <Yes> button 111, the detection threshold of the center image display is taken over and the user goes back to dialog 100.

By operating cancel button 39 change in dialog 100, all changes made are rejected and the user goes back to optimization dialog 90 (see FIG. 11).

Figure 16:
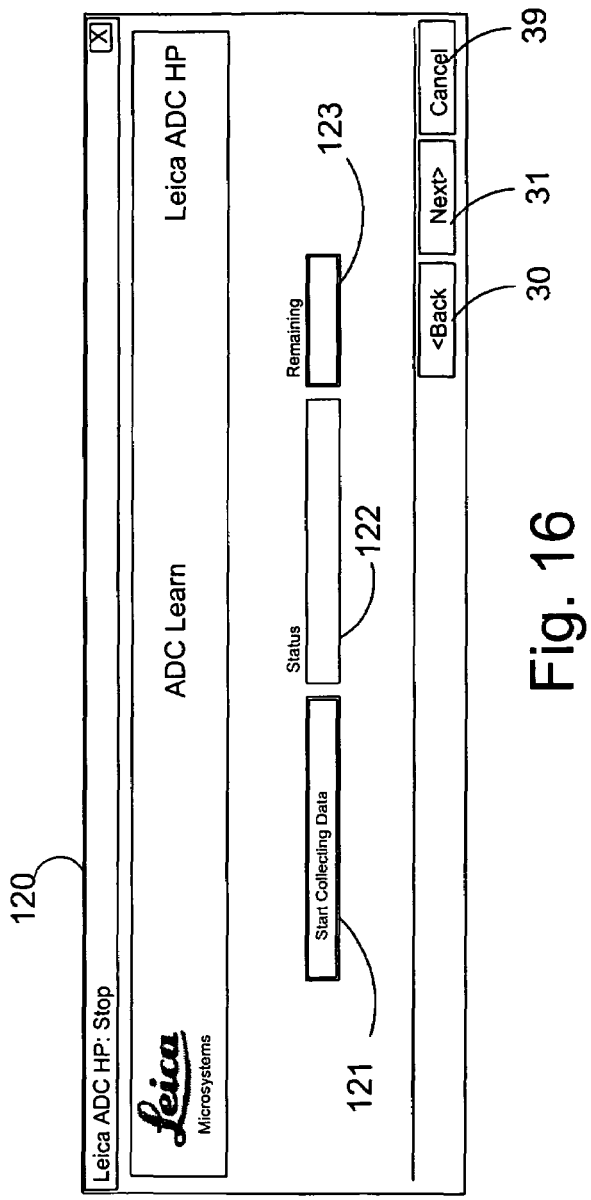
FIG. 16 shows a page of the learning mode by which the user carries out an automatic generation of a knowledge base.

FIG. 16 shows page 120 of the learning mode, by which the user carries out an automatic generation of a knowledge base. With start collecting data button 121, all the necessary data for all defects of all selected wafers are accepted and recorded.

The status is displayed to the user in Statusbox 122 and Infobox 123. Infobox 123 displays the defects "yet to be processed" from the total number (e.g. "267 of 750"). Operating back button 30 is not allowed when the data acceptance procedure is running. Operating next button 31 is also not allowed if the data recording procedure is running. Operation of cancel button 39 is not allowed when the data recording procedure is running. If the actuation of cancel button 39 is allowed, all open files will be closed and deleted.

The sequence is as follows: The Viscon sequencer is started again and all defects of the input file are selected. In a first step, defects on the wafer or wafers are approached, pictures are taken, descriptors generated and stored in the ADC result data on the defect. The pictures of the defects will be stored with the following settings:

"Write to Archive File"
"All Images"
"Image Compression": yes
"Leica-ImageStore": no In a second step, the Viscon sequencer pauses on the basket level (before storing the output file).

In a third step, the generation of the groups from the collection of descriptors occurs ("pregrouping").

In a fourth step, the pregrouping attempts to create a maximum of 20 groups. Groups with less than two examples are rejected. The resulting groups are copied temporarily to the knowledge base, whereby the defect code and defect description of each group are "numbered" for the first time (1, 2, 3, etc., or EasyClass1, EasyClass2, EasyClass3, etc.)

Figure 17:
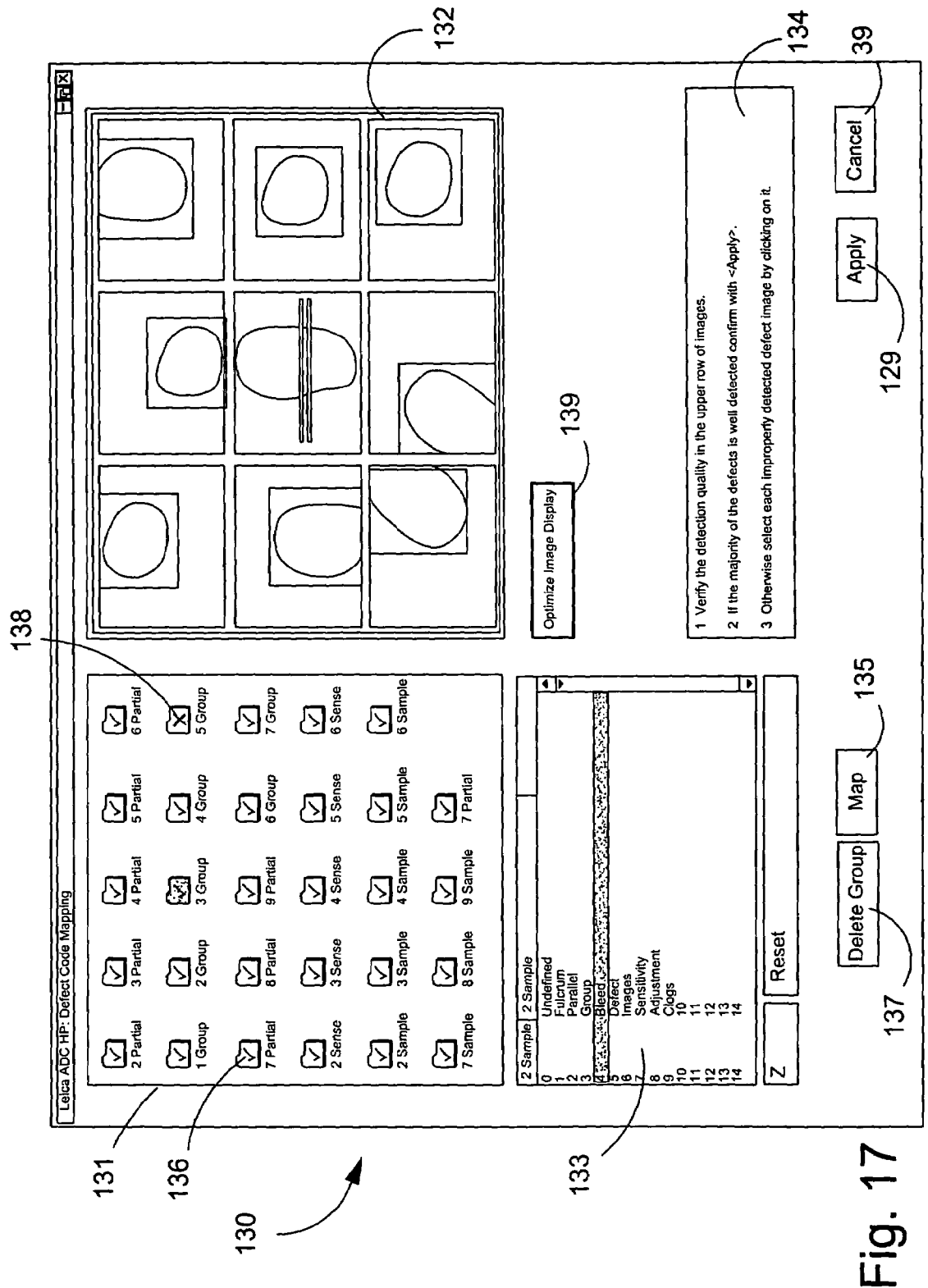
FIG. 17 shows a representation of the "defect code mapping" dialog.

In a fifth step, dialog 130 is displayed for dividing the defects i.e. "defect code mapping" (see FIG. 17). "Defect code mapping dialog" 130 is essentially represented by first window 131, a second window 132, third window 133 and a fourth window 134. In first window 131, a binder icon is shown for each group generated in the fourth step. Window 132 displays the pictures of the first nine examples of the selected group in a thumbnail representation. Window 133 displays the actual defect code table. By selecting a defect code and pressing <Map> button 135, this code is assigned to the selected classes. The icon of this class changes in that it gets a green hook 136 and the corresponding defect code text is displayed. This "mapping" can also be executed by a double click in the defect code table. When <Delete Group> button 137 is pressed, the currently displayed group is marked for deletion. The corresponding binder icon gets a red cross 138.

When pressed, toggle button 139 designated with "optimize image display" makes it possible for a section around the defect marking in original size of the example pictures to be shown. If the defect marking in an example picture is too large, the display does not change. By pressing toggle button 139 on again, you go to the reduced full picture display. Operation of apply button 129 is allowed if all defect groups have been handled, i.e., mapped or marked for deletion.

Figure 18:
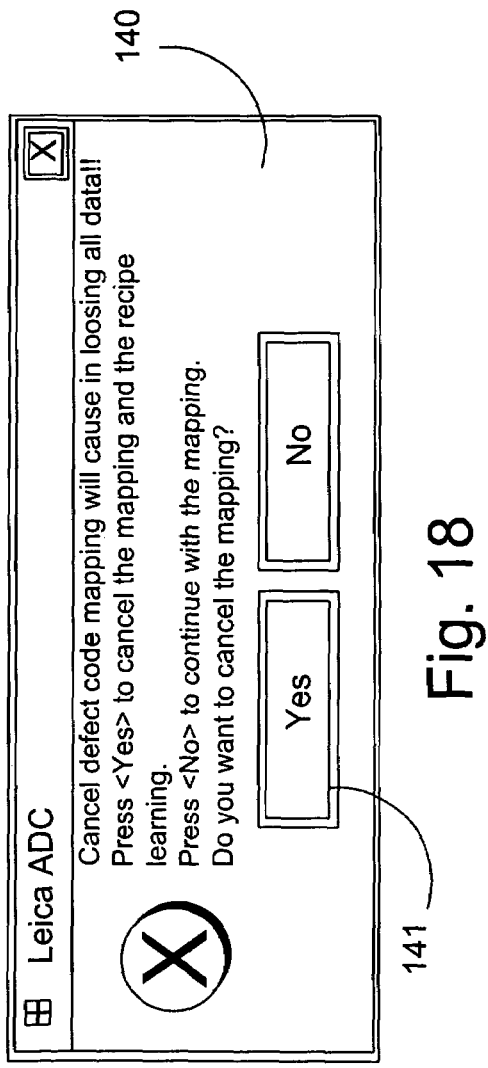
FIG. 18 shows a representation of an information dialog.

In a sixth step, there is an attempt to reduce the number of individual examples per mapped group (groups marked as for deletion will not be used and rejected). This is necessary so that specific groups with a lot of defects do not dominate the knowledge base and defects can preferably be assigned to this class. The result is taken over into the knowledge base, and the user comes to the ADC learning mode during operation of cancel button 39 on display 11 of information dialog 140 shown in FIG. 18. After operating <Yes> button 141, the "mapping" in the entire ADC learning mode will be canceled.

Figure 19:
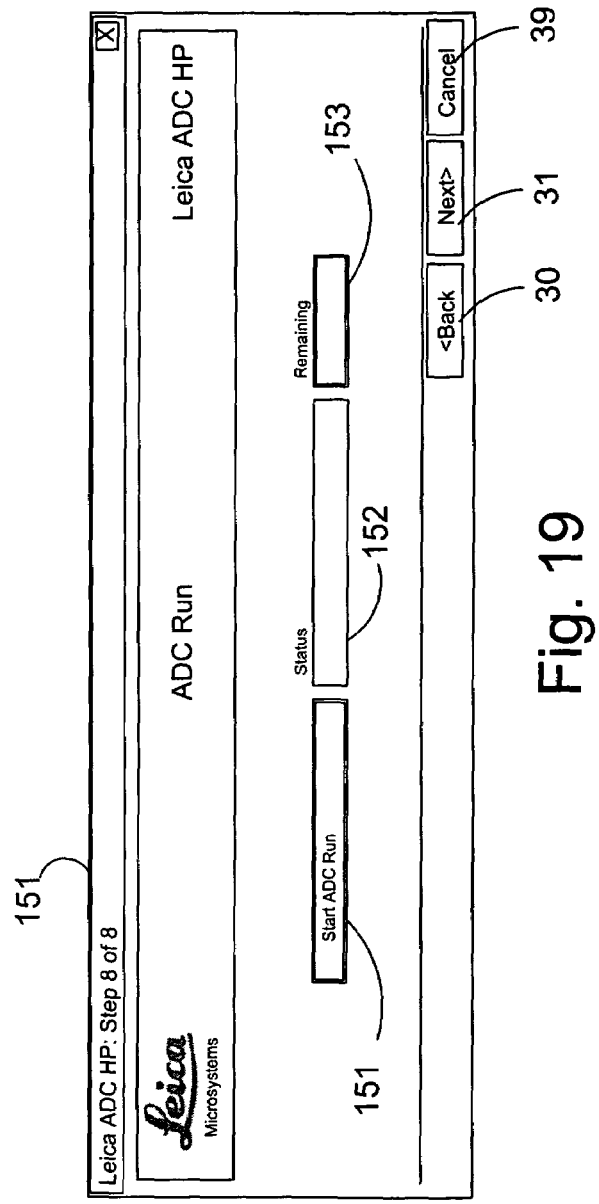
FIG. 19 shows a representation of a dialog for starting the "ADC run"

FIG. 19 shows a representation of a dialog 150 for starting an ADC run. With a start ADC run button 151, after button 151 is pressed there is a classification of all defects of the selected wafers "offline" (i.e., without approaching them again). The classification is carried out with the current ADC knowledge base. Dialog 150 includes a Statusbox 152 and Infobox 153. The display of the defects yet to be classified of the total number is displayed in Statusbox 153 (e.g., "123 of 750").

Operation of back button 30 is not permitted if Offline ADC is running. Operation of next button 31 is not permitted if Offline ADC is running. Also the operation of cancel button 39 is not allowed if Offline ADC is running. If the operation of cancel button 39 is allowed, all open files will be closed and deleted. If next button 31 was pressed, the sequencer is started again. The result data file is written and the sequencer ends automatically, whereby all files that are still open are closed.

Figure 20:
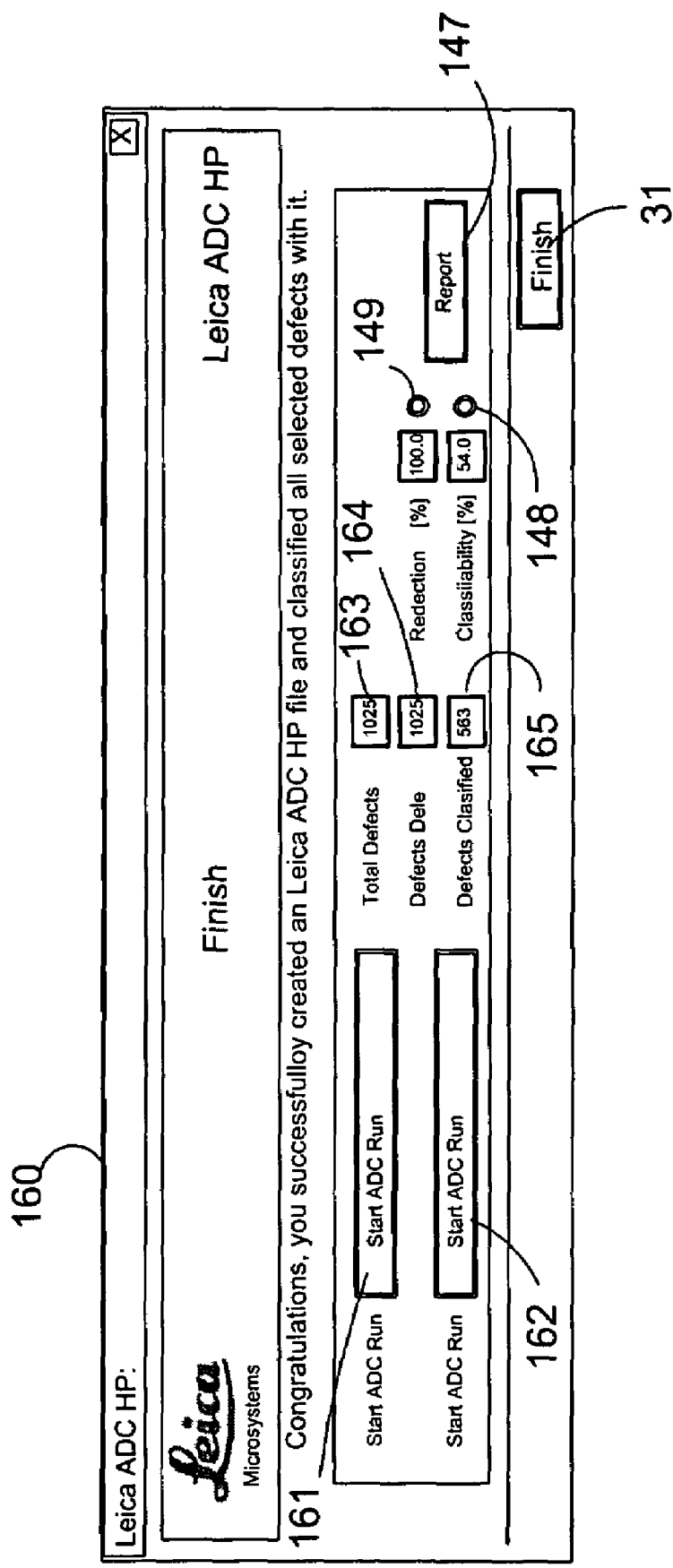
FIG. 20 shows a representation of a finish dialog.

FIG. 20 shows a representation of a dialog 160 which is the finish screen. An Infobox 161 is provided for an output file. Infobox 161 is used to display the stored data files. Only the file name is displayed.

The Easy ADC VSL file is also displayed in Read Only Editbox 162. The display of the generated "ADC run" file appears in Infobox 162. Only the file name is displayed. The complete path is displayed in a tool tip.

The number of "total defects" is displayed in Infobox 163. The total number of all defects can be read Infobox 163.

The "defects detected" will be displayed in Infobox 164. The "redetection" of the defects in percent will also be displayed in Infobox 166. The display of the defects detected with ADC is shown absolutely and as a percentage. LED 149 displays in color whether the percentage lies above the pre-defined value. If the value lies above the predefined value, LED 149 is green, otherwise LED 149 is red. The number of classified defects is displayed in Read Infobox 165. The percentage of classified defects "classifiability" is also shown in Infobox 167. The display of the defects classified with ADC is shown absolutely and as a percentage. LED 148 shows in color whether the percentage lies over a predefined value. Green means that the percentage lies over the predefined value. If the value lies below that, the display is red.

Figure 21:
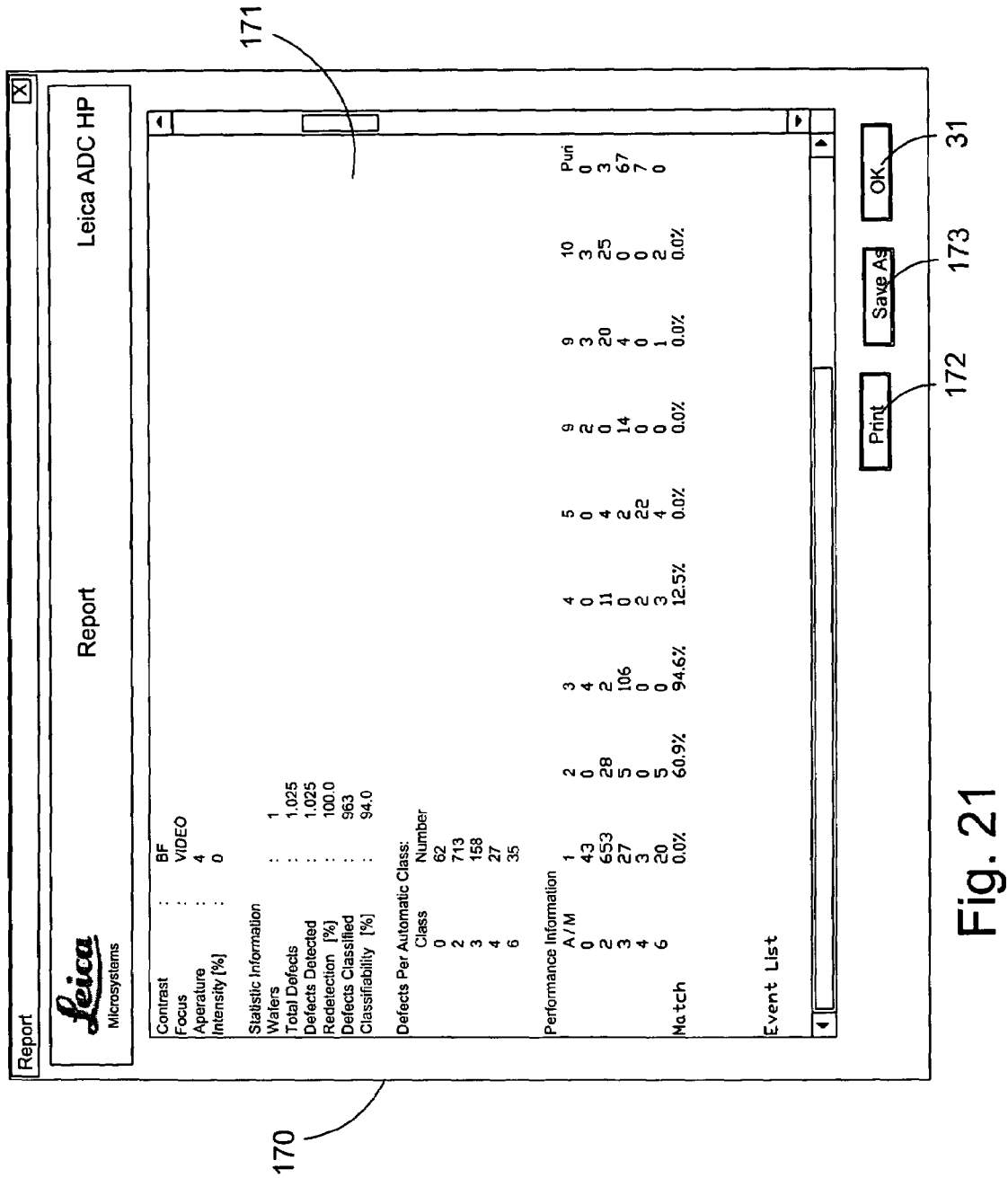
FIG. 21 shows a representation of a report dialog.

By operating a report button 147, a report dialog 170 is displayed (FIG. 21). Report dialog 170 is user-dependent. Another report is displayed only starting at the 'engineer' user level. The operation of finish button 146 will end the process.

FIG. 21 shows report dialog 170 with the expanded display of data in an Infobox 171. The following data are output: file information: (P) output file name (+path), recipe information: (P), ADC HP recipe file name (+path), knowledge base file name (+path), auto alignment file name (+path), focus type "LASER" or "VIDEO" with grab setup file names (+path), knowledge base information (A) (P), lens used, contrast method used, focus type, aperture used, light intensity used, statistical information (P), number of wafers, total number of defects, number of classified defects, number of ADC classes, defects per class (in matrix form), number of detected defects, absolute/percent, number of classified defects, absolute/percent, number of classifications per ADC defect class (P), performance information: (A) (P), accuracy, purity, confusion matrix (A) (P) and a defect list (A). A sorted table contains the following data per date record: the slot number, the event number, the manual classification, the ADC classification, the ADC classification with confidence value and the ADC classification with confidence value. In this case, only the first 300 entries are output. (A) means that these data are visible only in the expanded report. (P) means that the data can be printed out.

Report dialog 170 is provided with print button 171. A preview of the ADC HP report is displayed on display 11. The printout can be printed out using a standard printer. The printout is in landscape format since in portrait format the paths are usually not completely displayed or printed out.

FIG. 22 is a representation of a printed Easy ADC Report 180. When save button 173 is operated (see FIG. 21), the ADC HP report can be stored as a test file (extension TXT).

We claim:

1. A computer-based method for teaching a knowledge-based database for automatic defect classification, which comprises:
   (a) accepting, using a specially programmed computer, selecting a user selection of a review data file;
   (b) accepting, using the specially programmed computer, inputting parameters and data by a user on one page of a learning mode whereby the parameters and the data are known to the user;
   (c) starting, using the specially programmed computer, an alignment procedure and a procedure for adjusting light intensity, the alignment procedure with respect to at least one point on a wafer;
   (d) automatically adjusting, using the specially programmed computer, the optimal intensity of the light intensity accepting a selection of a first specific number of defects to approach on a first wafer and taking respective pictures of the first specific number of defects on the first wafer and if necessary regulating to the optimal illumination using the respective pictures;
   (e) checking, using the specially programmed computer, a detection, whereby an optimization of the detection parameters is carried out by accepting a selection of a second specific number of defects to approach on a second wafer, taking pictures of the second specific number of defects on the second wafer, displaying the pictures, and using the pictures to adjust a detection threshold using pictures;
   (f) automatically approaching all defects of a wafer or wafers, whereby the respective defect is detected and a descriptor is assigned, by the specially programmed computer, to the respective defect; and,
   (g) analyzing and automatically grouping, using the specially programmed computer, the descriptors of the defect.

2. The method according to claim 1, wherein the input of parameters and data further comprise the selection of elements present on a semiconductor substrate, wherein the elements can be memory circuits, logic circuits, a blank wafer without resist or with resist.

3. The method according to claim 2, wherein the parameters or data of layers on the wafer comprise the data of a polymer layer, an oxide layer, a contact or a metal layer.

4. The method according to claim 1, wherein the user selects a lighting type, at least one lens and a focus type.

5. The method according to claim 4, wherein bright field, UV or DUV is selected as the lighting type.

6. The method according to claim 4, wherein a default setting is bright field and the lens has a 100× magnification.

7. The method according to claim 4, wherein a manual two-point alignment is carried out; wherein a first point is aligned manually by approaching a table; wherein during the teaching of the first point, data is automatically stored for the auto alignment file; and each alignment point is taught with three different magnifications of the lens.

8. The method according to claim 1, wherein the adjusting of the optimal intensity of illumination is achieved by random selection of a specific number of defects; approaching the selected defects; taking a picture of each defect; whereby a start value for the brightness of the illumination and adjustment of the illumination is achieved using a histogram evaluation.

9. The method according to claim 8, wherein defects that are no larger than 25% of a video image width and height are used to adjust the optimal intensity of the illumination.

10. The method according to claim 8, wherein 20 defects are used to adjust the intensity of the illumination.

11. The method according to claim 1, wherein the defects on the wafer that are automatically approached, have pictures taken which are temporarily stored until pictures are taken of all the defects.

12. The method according to claim 11, wherein after all the pictures are taken, they are shown on a display as thumbnails.

13. The method according to claim 12, wherein a few thumbnails are rejected if the thumbnails exceed a threshold value for the focus.

14. The method according to claim 1, wherein the analysis and automatic grouping of the descriptors of the defects divides the thumbnails of the defects recorded into groups, and on the display the first nine examples of a selected group of defects are displayed in a thumbnail representation.

* * * * *

UNITED STATES PATENT AND TRADEMARK OFFICE
CERTIFICATE OF CORRECTION

PATENT NO. : 7,623,698 B2  Page 1 of 1
APPLICATION NO. : 10/564454
DATED : November 24, 2009
INVENTOR(S) : Soenksen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 815 days.

Signed and Sealed this

Twenty-sixth Day of October, 2010

David J. Kappos
*Director of the United States Patent and Trademark Office*